(12) United States Patent
Chang et al.

(10) Patent No.: US 10,883,975 B2
(45) Date of Patent: Jan. 5, 2021

(54) RESIDUAL TOXICANT DETECTION SYSTEM AND RESIDUAL TOXICANT DETECTION METHOD

(71) Applicant: INDUSTRIAL TECHNOLOGY RESEARCH INSTITUTE, Hsinchu (TW)

(72) Inventors: Chia-Jung Chang, Hsinchu (TW); Jui-Hung Tsai, Hsinchu (TW); Chih-Hao Hsu, Hsinchu (TW); Jing-Yuan Lin, Hsinchu (TW)

(73) Assignee: Industrial Technology Research Institute, Hsinchu (TW)

( * ) Notice: Subject to any disclaimer, the term of this patent is extended or adjusted under 35 U.S.C. 154(b) by 293 days.

(21) Appl. No.: 15/613,505

(22) Filed: Jun. 5, 2017

(65) Prior Publication Data

US 2018/0143173 A1    May 24, 2018

Related U.S. Application Data

(60) Provisional application No. 62/423,818, filed on Nov. 18, 2016.

(30) Foreign Application Priority Data

Feb. 15, 2017   (TW) .............................. 106104870 A

(51) Int. Cl.
*G01N 33/02*    (2006.01)
*G01N 21/33*    (2006.01)
(Continued)

(52) U.S. Cl.
CPC .......... *G01N 33/025* (2013.01); *A23N 12/02* (2013.01); *A47J 43/24* (2013.01); *G01N 21/01* (2013.01);
(Continued)

(58) Field of Classification Search
CPC . A23N 12/02; A47J 43/24; G01N 2021/3166; G01N 21/01; G01N 21/33;
(Continued)

(56) References Cited

U.S. PATENT DOCUMENTS 7,394,389 B2    7/2008   Nelson
7,423,751 B2    9/2008   Hairston et al.
(Continued)

FOREIGN PATENT DOCUMENTS

CN    1544916    11/2004
CN    1904596    1/2007
(Continued)

OTHER PUBLICATIONS

Taiwanese Office Action for Taiwanese Patent Application No. 106104870 dated Nov. 24, 2017, 7 Pages.
(Continued)

*Primary Examiner* — Dana Ross
*Assistant Examiner* — Joseph W Iskra
(74) *Attorney, Agent, or Firm* — JCIPRNET

(57) ABSTRACT

Provided is a residual toxicant detection system and a residual toxicant detection method, the residual toxicant detection method including: allowing an aqueous solution containing a residual toxicant to flow into a detection portion including a cavity; providing at a side of the cavity a light containing a specific wavelength range to react with the residual toxicant; receiving the light that passes through the cavity on another side of the cavity, thereby generating a sensing signal; and calculating an amount of change in absorbance of the aqueous solution according to the sensing signal, wherein when the amount of change in absorbance is less than a threshold value, a detection count is accumulated, and when the accumulated detection count is greater than a predetermined value, a detection result is generated. There-
(Continued)

fore, whether or not the residual toxicant on the object is cleaned can be determined easily and accurately.

24 Claims, 7 Drawing Sheets

(51) Int. Cl.
    *A23N 12/02*     (2006.01)
    *A47J 43/24*     (2006.01)
    *G01N 21/01*     (2006.01)
    *G01N 21/31*     (2006.01)
    *G01N 21/85*     (2006.01)

(52) U.S. Cl.
    CPC .............. *G01N 21/33* (2013.01); *G01N 21/85* (2013.01); *G01N 2021/3166* (2013.01)

(58) Field of Classification Search
    CPC ...... G01N 21/85; G01N 33/025; G01N 21/31; G01N 2021/3125; G01N 2021/3129–3155; G01N 2021/0193; G01N 21/3577; G01N 33/188; G01N 21/532; G01N 21/59
    USPC .......................................................... 99/492
    See application file for complete search history.

(56) References Cited

U.S. PATENT DOCUMENTS

| | | | |
|---|---|---|---|
| 7,525,660 | B2 | 4/2009 | Gigioli et al. |
| 9,568,458 | B2 * | 2/2017 | Smeeton .............. G01N 21/532 |
| 2007/0192041 | A1 | 8/2007 | Goldstein et al. |
| 2015/0185153 | A1 | 7/2015 | Zhang et al. |
| 2016/0054281 | A1 * | 2/2016 | Smeeton .............. G01N 21/532 |
| | | | 250/373 |
| 2016/0305889 | A1 | 10/2016 | Yoshikawa et al. |
| 2018/0059015 | A1 * | 3/2018 | Li ...................... G01N 21/3577 |

FOREIGN PATENT DOCUMENTS

| | | |
|---|---|---|
| CN | 102384890 | 3/2012 |
| CN | 102519916 | 6/2012 |
| CN | 102628810 | 8/2012 |
| CN | 103257206 | 8/2013 |
| CN | 103543180 | 1/2014 |
| CN | 103630509 | 3/2014 |
| CN | 103808948 | 5/2014 |
| CN | 104062449 | 9/2014 |
| CN | 204154651 | 2/2015 |
| CN | 105181681 | 12/2015 |
| CN | 204903390 | 12/2015 |
| CN | 105891200 | 8/2016 |
| CN | 106033070 | 10/2016 |
| TW | M506286 | 8/2015 |

OTHER PUBLICATIONS

Xia, et al. "Nanomaterials-Based Optical Techniques for the Detection of Acetylcholinesterase and Pesticides", Sensors 2015, 15 (Basel), DOI: 10.3390/s150100499, Dec. 30, 2014, 499-514.
Cesarino, et al. "Electrochemical detection of carbamate pesticides in fruit and vegetables with a biosensor based on acetylcholinesterase immobilised on a composite of polyaniline-carbon nanotubes", Food Chemistry, Dec. 1, 2012, 373-879.
Teye, et al. "Review on the Potential Use of Near Infrared Spectroscopy (NIRS) for the Measurement of Chemical Residues in Food", American Journal of Food Science and Technology, 2013, vol. 1, No. 1, DOI: 10.12691/ajfst-1-1-1, May 1, 2013, 1-8.
Armenta, et al. "Capillary liquid chromatography with off-line mid-IR and Raman micro-spectroscopic detection: analysis of chlorinated pesticides at ppb levels", Analytical and Bioanalytical Chemistry vol. 397, Issue 1, May 2010, 297-308.
Chinese Office Action for Chinese Patent Application No. 201710235670.5 dated Dec. 26, 2019.
"Office Action of China Counterpart Application", dated Jul. 31, 2020, pp. 1-8.

* cited by examiner

RESIDUAL TOXICANT DETECTION SYSTEM AND RESIDUAL TOXICANT DETECTION METHOD

BACKGROUND

1. Technical Field

The present disclosure relates to a detection technique, and, more particularly, to a residual toxicant detection system and a residual toxicant detection method.

2. Description of Related Art

Food testing is currently carried out by sampling inspection. However, in the face of a variety of testing requirements, not every requirement can be covered. With the current emphasis on food safety, detection of residual toxicants has become very important. For example, fruits and vegetables may have residual pesticides thereon, but few people carry out tests to see if residual pesticides are on the fruits and vegetables. Long-term consumption of pesticide residues in fruits and vegetables may have adverse effect on the human bodies.

At present, common methods of rapid detection of pesticides include bioassay and spectroscopic methods. For bioassay, farmers submit their fruits and vegetables to be tested a few days before harvesting. This rapid screening method is a biochemical enzyme inhibition method, which requires a fixed sample sampling and biochemical enzyme reaction, but it is not popular among consumers. Second, the current use of bioassay is only targeted at the detection of organic phosphorus and carbamate. It also has a certain degree of inaccuracy (false negative—35%, pseudo-positive—50%). Thus, it cannot reliably detect pesticides, especially those that are banned. In addition, the use of bioassay method for household detection requires a series of complicated actions like those performed in a laboratory, and it is thus not suitable for general households use.

In the spectroscopic method, spectral comparison is used to determine the type of pesticide and its concentration. However, there are currently more than 300 different types of registered pesticides, and it is increasingly difficult to carry out database comparison. In other words, a large number of comparisons are needed, which led to difficult detection. Moreover, quantitative sampling is unavoidable, which is also not acceptable for general consumers. LC/MS/MS (i.e., Liquid chromatography (LC) and mass spectrometers (MS) used in series) or high performance liquid chromatography (HPLC) that are used by government agencies are expensive and time consuming. As a result of this, they are not widely used.

It can be seen from the above that the existing techniques used in pesticide detection usually have poor accuracy and small pesticide detection coverage. Therefore, a rapid detection technique applicable to home testing is needed that helps users to monitor the removal of residual pesticides without damaging the tested objects or requiring complicated quantitative sampling actions.

SUMMARY

The present disclosure provides a residual toxicant detection system, which may include: a light source module including at least one light source emitter and at least one light sensor, wherein the at least one light source emitter emits a light having a specific wavelength range; a detection portion including an inlet, an outlet and a cavity, wherein an aqueous solution containing a residual toxicant flows into the inlet, passes through the cavity, and flows out of the outlet for the residual toxicant to react with the light having the specific wavelength range, and the at least one light sensor receives the light having the specific wavelength range that passes through the cavity to produce a sensing signal; and a processing module configured to calculate an amount of change in absorbance of the aqueous solution based on the sensing signal, wherein when the amount of change in absorbance of the aqueous solution is less than a threshold, the processing module increases an accumulated detection count, and when the accumulated detection count is greater than or equal to a predetermined value, the processing module produces a detection result.

The present disclosure further provides a residual toxicant detection method, which may include: allowing an aqueous solution containing a residual toxicant to flow into a detection portion including a cavity; providing at one side of the cavity a light having a specific wavelength range to react with the residual toxicant; receiving the light having the specific wavelength range at another side of the cavity to produce a sensing signal; and calculating an amount of change in absorbance of the aqueous solution based on the sensing signal, wherein when the amount of change in absorbance of the aqueous solution is less than a threshold, an accumulated detection count is increased, and when the accumulated detection count is greater than or equal to a predetermined value, a detection result is produced.

BRIEF DESCRIPTION OF THE DRAWINGS

The present disclosure can be more fully understood by reading the following detailed description of the embodiments, with reference made to the accompanying drawings, wherein.

DETAILED DESCRIPTION OF THE EMBODIMENTS

The present disclosure is described by the following specific embodiments. Those with ordinary skills in the arts can readily understand other advantages and functions of the present disclosure after reading the disclosure of this specification. The present disclosure may also be practiced or applied with other different implementations. Based on different contexts and applications, the various details in this specification can be modified and changed without departing from the spirit of the present disclosure.

Figure 1:
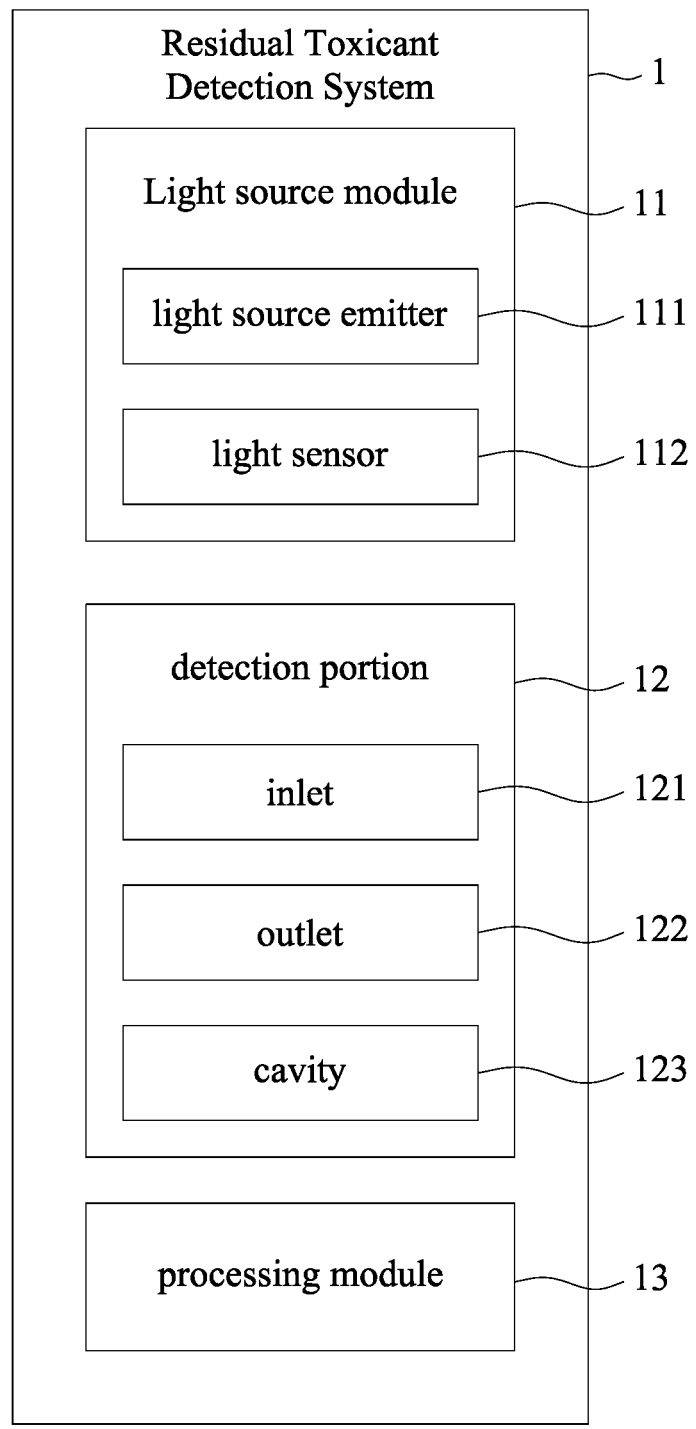
FIG. 1 is a diagram illustrating a system framework for a residual toxicant detection system in accordance with the present disclosure.

In an embodiment, referring to FIG. 1, which shows a diagram illustrating a system framework for a residual toxicant detection system 1 in accordance with the present disclosure, the residual toxicant detection system 1 can be laid out as a single apparatus for testing residual toxicants on fruits and vegetables, include a light source module 11, a detection portion 12, and a processing module 13.

The light source module 11 includes at least one light source emitter 111 and at least one light sensor 112. The light source emitter 111 may emit light at a specific wavelength range. In an embodiment, the residual toxicant detection system 1 of the present disclosure tests for residual toxicants through a light sensing mechanism, and the light source emitter 111 is capable of emitting light at a specific wavelength range.

In order to detect various types of toxicants, the light proposed by the present disclosure may have different specific wavelength ranges. In other words, there can be a plurality of light source emitters 111, and the same or different amount of the light sensors 112 can be provided correspondingly.

In an embodiment, the specific wavelength range may be 220-240 nm, 250-270 nm, or 270-290 nm.

The detection portion 12 includes an inlet 121, an outlet 122 and a cavity 123. The light source emitter 111 and the light sensor 112 are disposed at the two sides of the cavity 123, respectively. An aqueous solution containing a residue toxicant is directed into the inlet 121 and out of the outlet 122 through the cavity 123. In an embodiment, the detection portion 12 can be designed to have a tubular shape, including the inlet 121 at one end, the outlet 122 at the other end, and the cavity 123 through which the aqueous solution runs. In order to conduct the detection, the light source emitter 111 and the light sensor 112 are disposed at the two sides of the cavity 123, respectively. Therefore, the light emitted by the light source emitter 111 passes through the cavity 123 and is received by the light sensor 112. However, the present disclosure is not limited as such. In other words, for example, the light source emitter 111 and the light sensor 112 can also be provided on the same side of the cavity 123, and the light emitted by the light source emitter 111 is received by the light sensor 112 after passing through the cavity 123 via a light reflector or other set of mirrors.

When the aqueous solution containing a residual toxicant flows through the cavity 123, the residual toxicant reacts with the light at the specific wavelength range. The light sensor 112 receives the light at the specific wavelength range passing through the cavity 123, and finally the light sensor 112 produces a sensing signal.

The processing module 13 is used for calculating the amount of change in absorbance of the aqueous solution containing the residual toxicant based on the sensing signal. When the amount of change in absorbance of the aqueous solution containing the residual toxicant is less than a threshold, an accumulative detection count is increased. When the accumulative detection count is greater than or equal to a predetermined value, a test result is issued. In an embodiment, the processing module 13 analyzes the sensing signal and then obtains signal information regarding the residual toxicant in the aqueous solution. Before detection is performed, a calibration value (or background value) is obtained. This is a detection signal value obtained when no test object is present. With the toxicant detection value obtained from the sensing signal and the calibration value, the amount of change in the absorbance of the aqueous solution containing the residual toxicant can be determined, which is the change in the amount of the residual toxicant in the aqueous solution.

Thereafter, during continuous monitoring, if the amount of change in absorbance of the aqueous solution containing the residual toxicant is less than a predetermined threshold, an accumulative detection count is increased by one. This means that the amount of change in absorbance is small, and the residual toxicant presented in the tested object has been removed to a certain degree. However, in order to avoid the misjudgment of a single detection, the accumulative detection count is used. That is, when the amount of change in absorbance is lower than the threshold, the accumulative detection count is increased by one. Finally, as the accumulative detection count reaches a predetermined value, the removal of the residual toxicant on the tested object stops.

In another embodiment, the present disclosure proposes that the processing module 13 will generate a test result when the amount of change in absorbance of the aqueous solution has been continuously less than the threshold value for a certain amount of times. More specifically, the absorbance change of the aqueous solution being less than the threshold may happen continuously or discretely. In an embodiment, when the accumulative detection count has reached a certain number (a predetermined value), the removal of the residual toxicant on the tested object is regarded as stopped. In another embodiment, when the absorbance change in the aqueous solution has been continuously less than the threshold for a number of times in a row, for example, five times in a row, and a continuous accumulative count has reached five times, the removal of the residual toxicant on the tested object is regarded as stopped.

In the above detection mechanism, the absorbance change of an aqueous solution containing a residual toxicant is observed through continuous detection to determine the amount of residual toxicant, and when a plurality of detections or continuous detections meet the expected criteria, the removal of the residual toxicant on the tested object is determined to be ended. Therefore, the residual toxicant detection system 1 of the present embodiments has a convenient detection method, eliminating the need of comparison of large database containing a vast amount of toxicant information, thus the general public can perform this detection process with relative ease.

Figure 2:
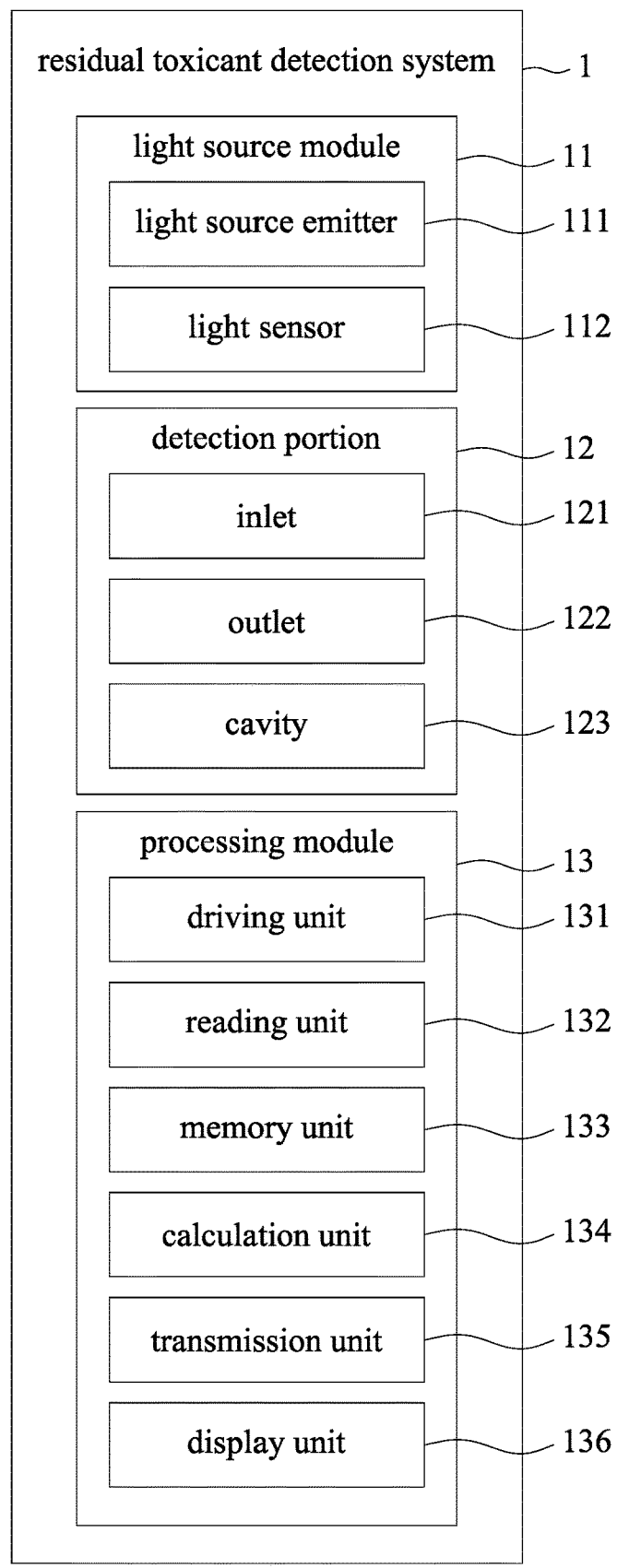
FIG. 2 is a diagram illustrating a system framework for a processing module of a residual toxicant detection system in accordance with the present disclosure.

Referring to FIG. 2, a diagram illustrating a system framework for a processing module of a residual toxicant detection system 1 in accordance with the present disclosure is shown. The residual toxicant detection system 1 is used for testing residual toxicants. The light source emitter 111 and the light sensor 112 in the light source module 11 and the inlet 121, the outlet 122 and the cavity 123 in the detection portion 12 are similar to those described in FIG. 1, further descriptions thereof hereby omitted.

The processing module 13 may include functions such as numerical value storing, reading, calculations, driving of elements, external transmission, and outcome display. In other words, in actual implementations, the processing module 13 can be designed as a microcontroller with multiple functions, and can be used to control the system with the cooperation of other circuits.

In an embodiment, the processing module 13 further includes a driving unit 131, a reading unit 132, a memory unit 133, a calculation unit 134, a transmission unit 135 and a display unit 136.

The driving unit 131 can be used for driving various elements, including the on/off of the light source emitter 111. As described before, there can be a plurality of light source emitters 111, so the driving unit 131 may choose to turn on or turn off of the light source emitters 111. In addition, under the demand for continuous sensing, the light source emitters 111 may intermittently emit light, or the light sensors 112 may intermittently sense light, which is also controlled by the driving unit 131. The driving unit 131 may also drive other modules or circuits if needed.

The reading unit 132 can be used for reading a sensing signal at a fixed time interval. The reading unit 132 primarily receives the sensing signal from the light sensor 112. As described before, the driving unit 131 controls the light source emitter 111 and the light sensor 112 so they perform their functions at fixed time intervals. Alternatively, the light source emitter 111 and the light sensor 112 can be continuously turned on, and the reading unit 132 reads the sensing signal at a fixed time interval. This also produces values at an interval.

The memory unit 133 can be used for storing the sensing signal. For subsequent data calculation, such as calculating an average, the sensing signal is stored by the memory unit 133.

The calculation unit 134 can be used for calculating the amount of change in absorbance based on the sensing signal and the calibration value to produce a detection result. The calculation of the amount of change in absorbance of the aqueous solution and degradation operation and determining of a monitored value obtained under continuous monitoring will be further illustrated below.

As described before, before detection, a calibration value (or background value in terms of voltage or power) can be obtained. A detection signal value obtained when no tested object is present. Equation (1) can be used to calculate the absorbance.

$$\text{Absorbance} = -20 \times \log(\text{detection value}/\text{calibration value}) \quad \text{Eqn. (1)},$$

wherein −20 must be negative, that is, negative is necessary, and 20 is an adjustable value; the detection value is the signal value obtained during detection of the light sensor (may be expressed in terms of voltage or power).

In addition, regarding degradation operation and determining, the present disclosure may perform detection at a fixed interval, that is, X absorbance calculation results are obtained. When X data are obtained, an average thereof is first obtained, and each data is subtracted from the average to obtain the change of the respective data relative to the average. For example, an average is taken with every ten data.

When the amount of change is less than a threshold Y, the amount of change relative to the average is small, and a record is increased by one. For example, Y can be set according to system requirements. For example, Y can be 0.05 dB. Finally, when Z data are accumulated, it is considered that the removal of the residual toxicant in the tested object has stopped. In an embodiment, the accumulation is a continuous accumulation, that is, when Z continuous data are accumulated, it is determined that the removal of the residual toxicant in the tested object has stopped.

The transmission unit 135 can be used for transmitting the detection result to an external device (not shown). The external device can be an electronic apparatus such as a mobile phone, a micro-computer, a tablet PC, a laptop or the like. Since the residual toxicant detection system 1 can be provided as a single apparatus, in order to provide users with a better operating mode and real-time notification, the transmission unit 135 can be connected with the external device. In actual implementations, the external device may control the operations of the residual toxicant detection system 1, and the final detection result can also be transmitted back to the external device.

In another aspect, some of the calculation determination mechanisms can be carried out by the external device. In this case, the residual toxicant detection system 1 may return a sensing data converted from the sensing signal or the change in absorbance to the external device, and the determination as to whether the removal residual toxicant in the tested object has stopped may reside in the external device. Therefore, the transmission unit 135 provides the connection with the external device. Whether data is to be calculated in the residual toxicant detection system 1 or the external device can be adjusted depending on the needs.

The display unit 136 can be used to display the detection result. In contrast to transmitting the detection result to the external device for display, users may also choose to have the result displayed on the detection apparatus via the display unit 136.

In addition, the calculation unit 134 may also produce a removal terminating signal based on the detection result. This removal terminating signal asks the driving unit 131 to stop the detection carried out by the residual toxicant detection system 1.

In conclusion, the present disclosure does not need to know what the type of the specimen (toxicant) is in advance. When a tested object is rinsed by water and by detecting the change in absorbance of the aqueous solution containing the specimen (toxicant), the efficiency of the removal of the residual toxicant can be known. When the tested object is continuously being rinsed, the absorbance of the aqueous solution containing the residual toxicant will vary. When this change in absorbance is less than a predetermined threshold, and such event has occurred many times or continuously occurred a predetermined number of times, the tested object is considered to be properly rinsed according to some safety standard.

Figure 3:
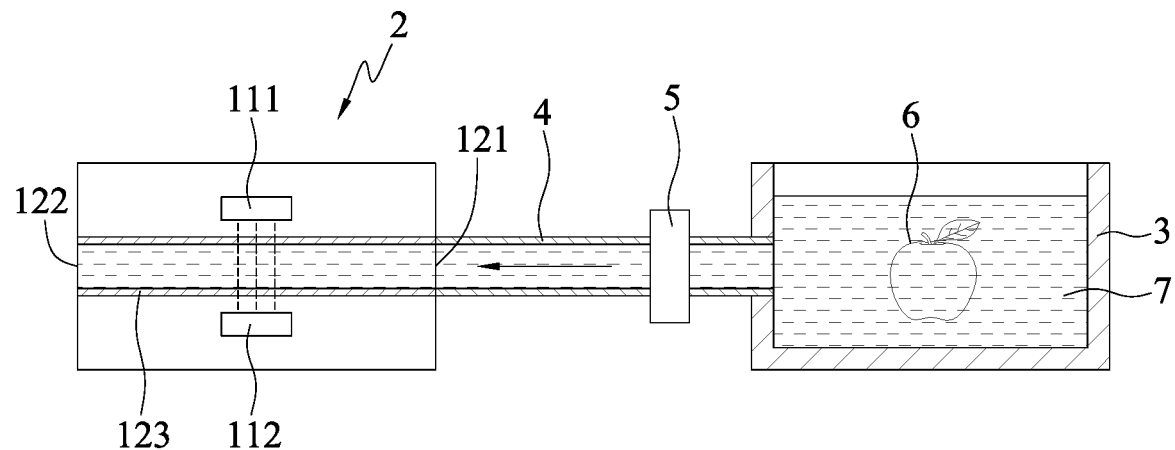
FIG. 3 is a schematic diagram illustrating a residual toxicant detection system in combination with a container in accordance with present disclosure.

In an embodiment, referring to FIG. 3, which shows a schematic diagram illustrating a residual toxicant detection system in combination with a container in accordance with present disclosure, the residual toxicant detection system can be combined with a fruit and vegetable rinsing machine, a detection apparatus 2 constructed from the residual toxicant detection system is connected with a container 3, and the inlet 121 is connected with the container 3. An object 6 to be tested containing residual toxicant(s) is placed inside the container 3, and an aqueous solution containing the residual toxicant(s) 7 flows into the detection apparatus 2.

In an embodiment, the detection apparatus 2 and the container 3 are connected via a conduit 4, and the aqueous solution containing the residual toxicant(s) 7 flows through the conduit 4 to the detection apparatus 2. The aqueous solution containing the residual toxicant(s) 7 flows into the inlet 121, passes through the cavity 123, and flows out from the outlet 122. The light source emitter 111 and the light sensor 112 are disposed at different sides of the cavity 123, respectively. The light emitted by the light source emitter 111 penetrates the cavity 123 and is received by the light sensor 112. As such, the light reacts with the aqueous solution containing the residual toxicant(s) 7.

Moreover, a pump 5 can be further provided between the container 3 and the inlet 121, which guides the aqueous solution containing the residual toxicant(s) 7 in the container 3 to the inlet 121. It should be noted that the role of the pump is to deliver the solution, and is an optional element. In addition, a filtering material (not shown) can be further provided between the container 3 and the inlet 121 for filtering impurities in the aqueous solution. When the detection apparatus 2 is carrying out detection, an external aqueous solution can be continuously added into the container 3, and the aqueous solution containing the residual toxicant(s) 7 can be discharged from a discharge hole (not shown) on the container 3 and/or the outlet 122. In another embodiment, the aqueous solution containing the residual toxicant(s) 7 discharged from the outlet 122 is returned into the container 3, because the present disclosure determines whether removal has terminated by detecting the change in absorbance.

Figure 7:
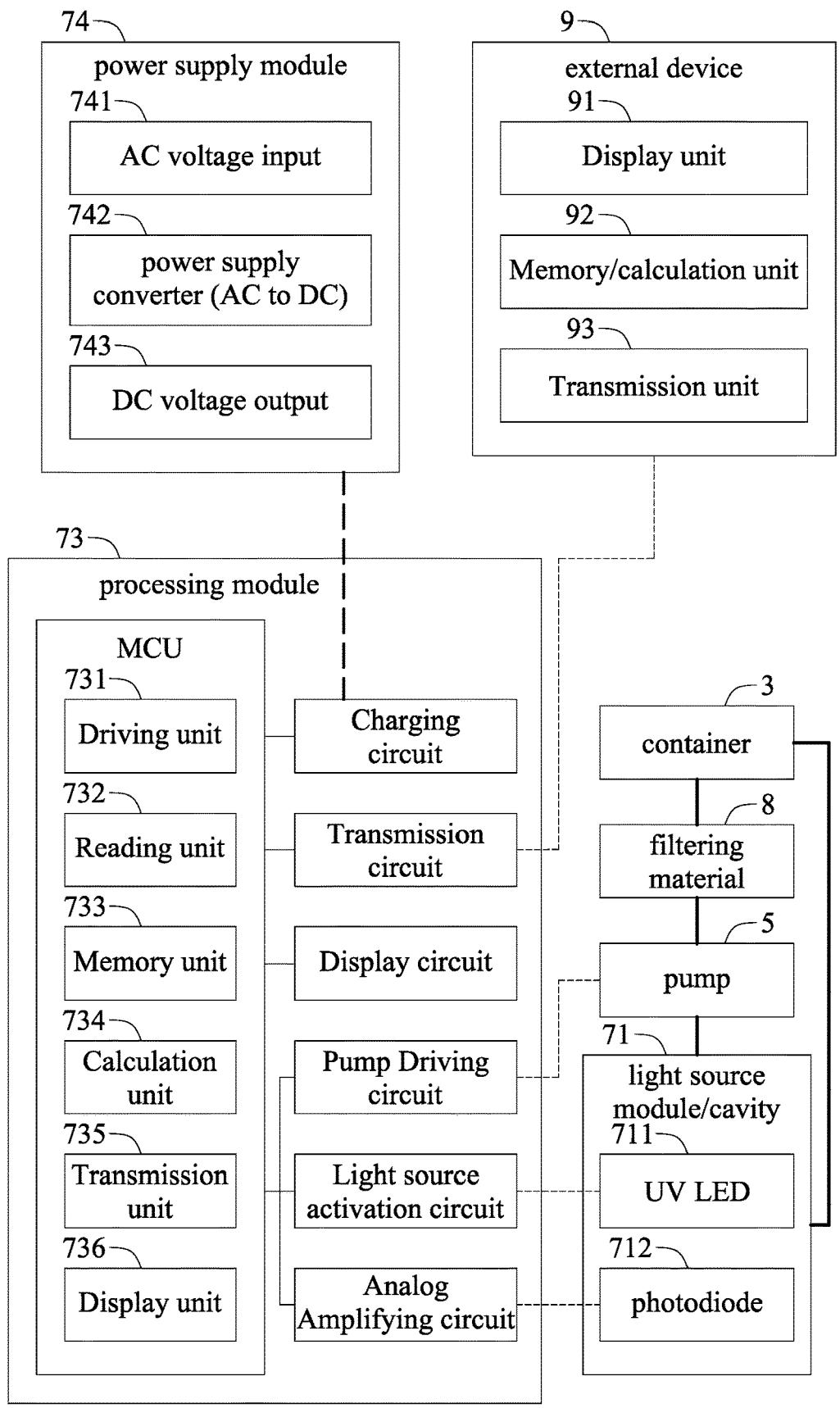
FIG. 7 is a schematic diagram depicting the structure composition of a residual toxicant detection system in accordance with the present disclosure in an actual implementation.

Furthermore, the entire detection apparatus 2 may include a power supply module connected to the processing module (as shown in FIG. 7) for providing the power necessary for operating the processing module. This is well known to those skilled in the art, and will not be further described.

Figure 4:
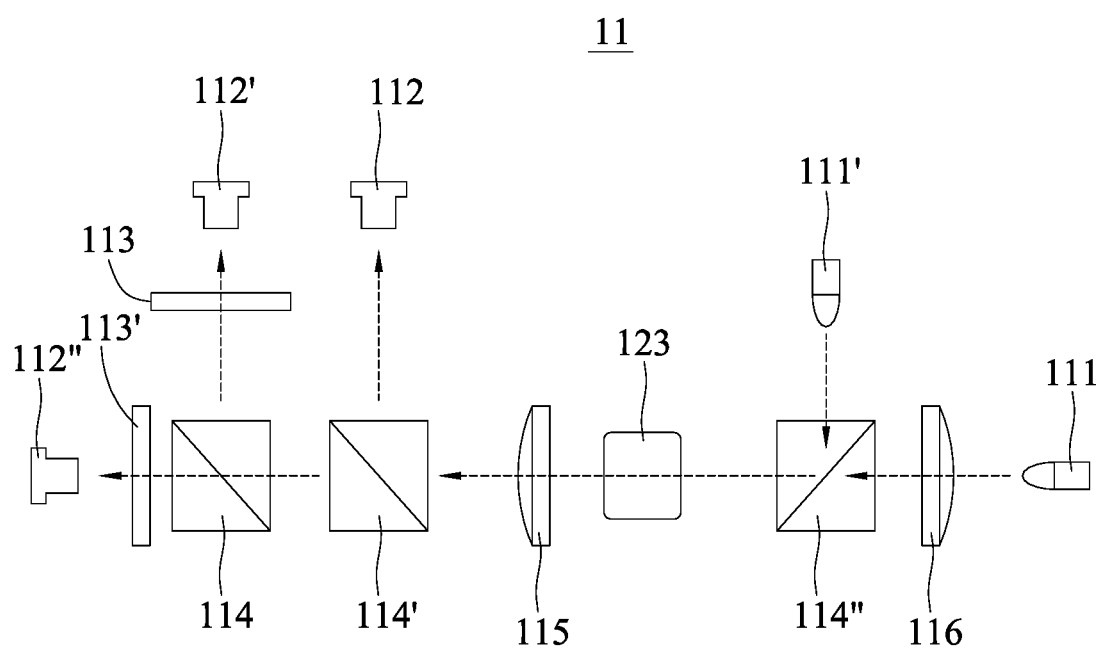
FIG. 4 is a schematic diagram of a light source module of a residual toxicant detection system in accordance with the present disclosure.

In an embodiment, referring to FIG. 4, which shows a schematic diagram of the light source module of a residual toxicant detection system in accordance with the present disclosure, the light source emitters and the light sensors in the light source module provide a light sensing mechanism for detecting the amount of toxicant in an aqueous solution. As shown in the diagram, a mirror set can be optionally added to light source emitters 111, 111', and light sensors 112, 112', 112'' are provided at two sides of the cavity 123, respectively. In order to detect the aqueous solution passing through the cavity 123, the plurality of light source emitters can provide light having different specific wavelength ranges. In addition, filters 113, 113' can be used to obtain light having different wavelength ranges. Moreover, a first spectral element 114 splits light having different wavelengths to the light sensors 112' and 112'', a second spectral element 114' splits light of different wavelengths (e.g. 280 nm or 250 nm) to the light sensors 112 and 112'', and a third spectral element 114'' guide incident light coming from different directions to the cavity 123. A focusing lens 115 focuses light to the second spectral element 114', and a collimator 116 collimates the light coming from the light source towards the third spectral element 114''.

Figure 5A:
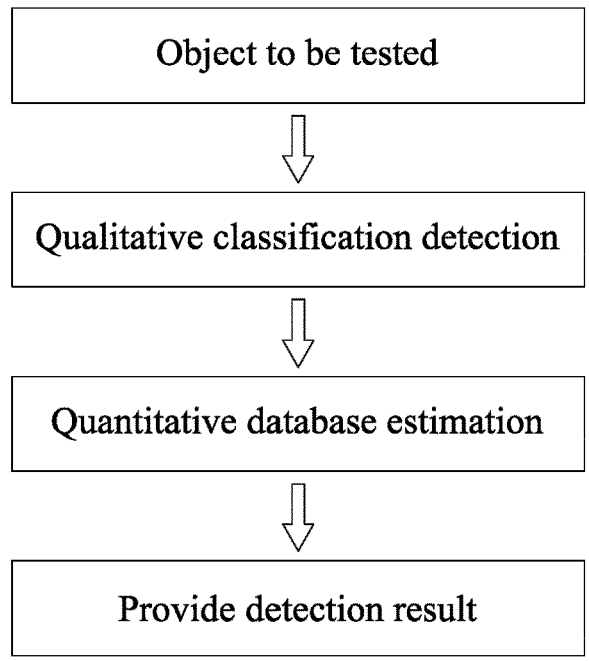
FIGS. 5A and 5B are diagrams illustrating differences between techniques of the prior art and the present disclosure.
Figure 5B:
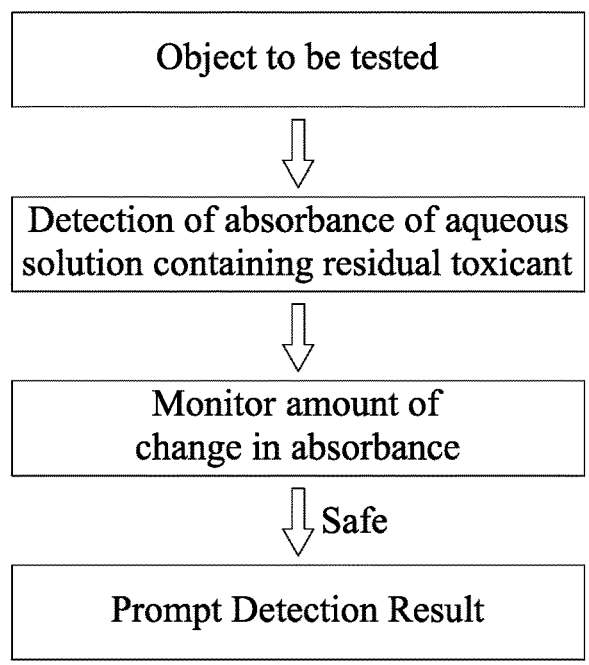

Referring to FIGS. 5A and 5B, differences between techniques of the prior art and the present disclosure are illustrated. As shown in FIG. 5A, a traditional approach requires qualitative classification detection to be performed, that is, determination of what type(s) of toxicant(s) is/are on an object to be tested, and then quantitative database estimation is performed to know the concentration of the toxicant based on pre-stored data in the database.

As shown in FIG. 5B, the method proposed by the present disclosure requires no qualitative detection to be performed in advance, by merely monitoring the change in absorbance of an aqueous solution containing residual toxicant(s), it is able to determine if the removal of the residual toxicant(s) in the tested object has stopped. In simple terms, testing of most of the water soluble pesticides will produce absorbed spectral bands, and the change in absorbance with time is then monitored. In this way, the present disclosure does not require a large qualitative classification database for comparison, and can thus be easily extended to the general households.

Figure 6:
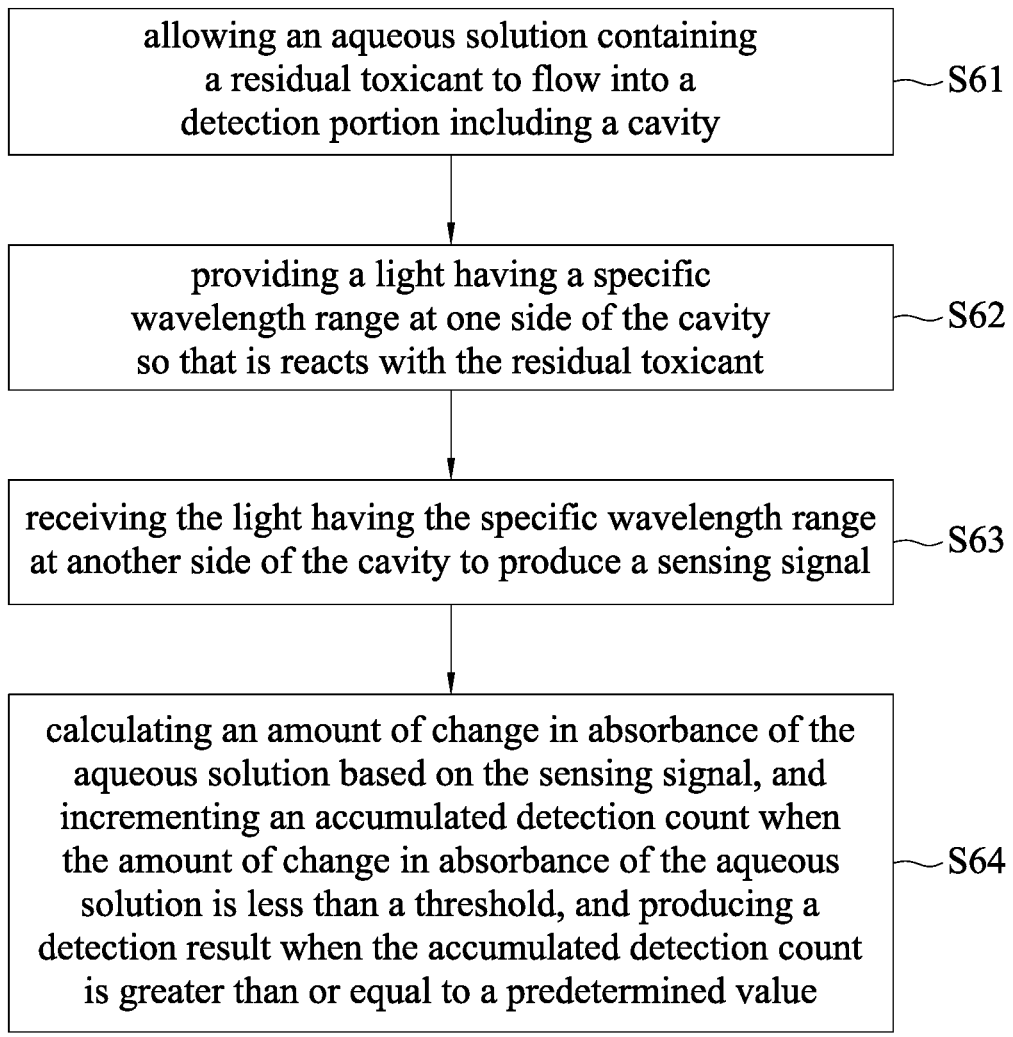
FIG. 6 is a diagram illustrating steps of a residual toxicant detection method in accordance with the present disclosure.

Referring to FIG. 6, a diagram illustrating steps of a residual toxicant detection method in accordance with the present disclosure is shown. More specifically, with the light sensing technique, the change in absorbance in an aqueous solution containing residual toxicant(s) can be obtained to determine whether the removal of the residual toxicant(s) on the tested object has terminated. When the residual toxicant detection system is performing the detection, an externally applied aqueous solution can be continuously added into the container 3 as shown in FIG. 3.

In step S61, an aqueous solution containing a residual toxicant flows into a detection portion containing a cavity. In actual implementations, a detection apparatus is designed as a detection portion with a cavity and the aqueous solution containing the residual toxicant to be tested is flowed pass the cavity.

In step S62, a light having a specific wavelength range is provided at one side of the cavity so that the residual toxicant reacts with the light having the specific wavelength range. The present disclosure determines the residual amount of a toxicant by the light sensing mechanism, so a light source emitter having a specific wavelength range is provided at one side of the cavity, and the light having the specific wavelength range, when penetrating the cavity, reacts with the residual toxicant in the aqueous solution.

Light can be a plurality of light having different specific wavelength ranges. In addition, the specific wavelength range may be 220-240 nm, 250-270 nm, or 270-290 nm.

In step S63, the light having the specific wavelength range is received at another side of the cavity to produce a sensing signal. Step S63 follows step S62. The light having the specific wavelength range penetrates the cavity, reacts with the residual toxicant in the aqueous solution, and is then received by a light sensor at another side of the cavity, and a sensing signal is produced. This sensing signal indicates the change in light intensity of the light caused by the residual toxicant.

In step S64, a change in absorbance of the aqueous solution is calculated based on the sensing signal, an accumulated detection count is increased when the change in absorbance is less than a threshold, and a detection result is produced when the accumulated detection count is greater than or equal to a predetermined value. In step S64, a change in absorbance of the aqueous solution is calculated based on the sensing signal, as described before, the absorbance is calculated with the help of a calibration value, and then the change in absorbance is calculated based on an average value of a plurality of record. For example, the difference between the average value and each sensed value can be used as the amount of change in absorbance. Thereafter, an accumulated detection count is increased by one when the change in absorbance of the aqueous solution is less than a threshold. In order to ensure its correctness, the present disclosure can produce a final detection result when the accumulated detection count is greater than or equal to a predetermined value.

In an embodiment, the disclosure also proposes that when the amount of the change in absorbance of the aqueous solution is continuously less than the threshold a predetermined number of times, the detection result is produced. In other words, the amount of the change in absorbance of the aqueous solution can be continuously or discontinuously less than the threshold, and the detection stops when the amount is less than the threshold. The disclosure also proposes that if the amount of the change in absorbance of the aqueous solution is continuously less than the threshold a predetermined number of times, the detection can be deemed as stopped.

The produced detection result can be transmitted to an external device, or displayed by the detection apparatus itself, or the termination signal is generated through the detection result to inform the detection apparatus to stop detection.

In an embodiment, the detection apparatus is connected to a container such as a household fruit and vegetable rinsing machines. Therefore, the aqueous solution containing the residual toxicant is from the container in which the object to be tested containing the residual toxicant is placed.

Referring to FIG. 7, a schematic diagram depicting the structure composition of a residual toxicant detection system in accordance with the present disclosure in an actual implementation is shown. A filtering material 8 for filtering and a pump 5 for assisting diversion can be provided between a container 3 (containing an object to be tested) and a light source module 71. An aqueous solution with a residual toxicant to be tested is guided out of the container 3.

In the actual implementation, the light source module 71 uses a UV LED 711 as a light source emitter and a photodiode 712 as a light sensor.

A power supply module 74 is connected with a processing module 73, and a thick dotted line between these two denotes the power supply circuit. The power supply module 74 may include an AC voltage input 741 connected to an external power supply, a power supply converter 742 for converting an AC voltage to a DC voltage, and a DC voltage output 743 for providing power output to be used by the processing module 73 during operations.

The processing module 73 is the processing core of the whole detection system. Thin solid lines between various elements in the processing module 73 denote internal circuits. A driving unit 731, a reading unit 732, a memory unit 733, a calculation unit 734, a transmission unit 735 and a display unit 736 can be embodied in software or firmware. These units make up a microcontroller (MCU), which provides functions such as internal calculation, control, driving, transmission etc. inside the processing module 73. Different circuit arrangements can be provided based on different functions in order to connect with or deliver information to other modules.

Thin dotted lines between the processing module 73 and other modules denote control/transmission circuits. A charging circuit is used for receiving power from the power supply module 74 and providing it to various units inside MCU. The transmission circuit can transmit a detection result after calculation to an external device 9. The display unit 736 is used for displaying a detection result on the detection apparatus, so a display circuit is activated when the display unit 736 is in operation.

The driving unit 731 controls the turning on/off of the UV LED in the light source module 71 through a light source activation circuit. A signal sensed by the photodiode is returned via an analog amplification circuit to the MCU. In addition, the MCU can also drive the pump 5 via a pump driving circuit.

The external device 9 includes a display unit 91, a memory/calculation unit 92 and a transmission unit 93. The processing module 73 exchanges data or information with the external device 9 via its transmission circuit. In other words, the external device 9 can be used to issue commands for controlling the processing module 73, or data of the processing module 73 can be delivered to the external device 9.

Figure 8:
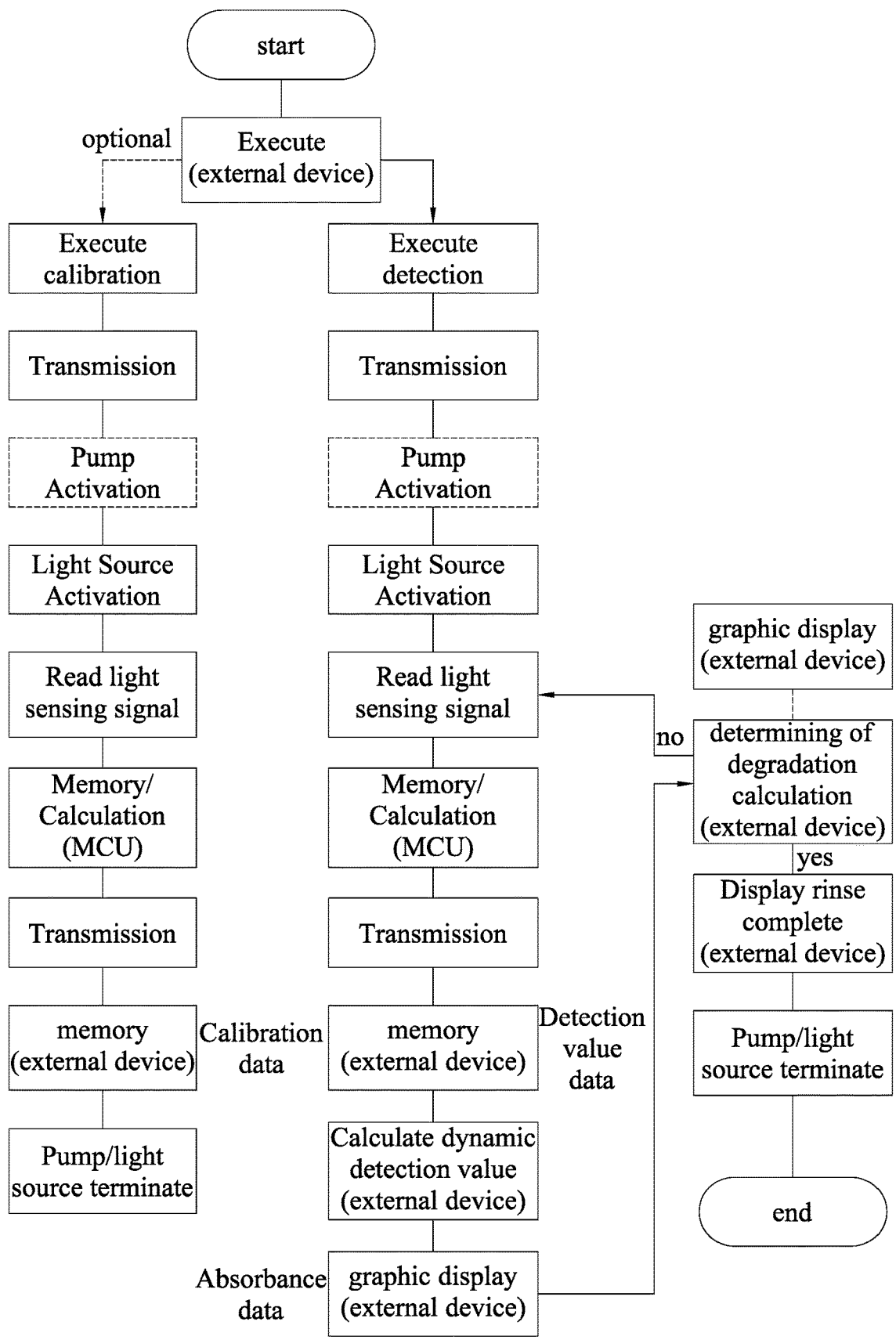
FIG. 8 is a flowchart illustrating a residual toxicant detection method in accordance with the present disclosure in an actual implementation.

Referring to FIG. 8, a flowchart illustrating a residual toxicant detection method in accordance with the present disclosure in an actual implementation is shown. The method in this embodiment is activated by an external device, and relevant calculations are performed by the external device. The "optional" flow on the leftmost column is carried out before actual detection, in which a calibration process is performed to obtain a calibration value (dotted lines indicate optional). A control command is transmitted; a light source and a pump are activated; the provision of the pump is optional depending on needs, a light sensor receives the sensing light provided by the light source; a MCU performs memory/calculation processes; and finally a calibration value is transmitted to the external device for storage and the light source and the pump are stopped. In the above steps, the calibration value is first obtained for subsequent calculation of absorbance.

The flow to the right indicates a detection is performed, in which a control command is transmitted; the light source and the pump are activated; the provision of the pump is similarly optional depending on needs, the light sensor receives the sensing light provided by the light source; the MCU then performs memory/calculation processes; a detection value is transmitted to the external device for storage; and the external device performs calculation on the dynamic detection value to obtain an absorbance data, which is similarly stored in the external device.

Next, the determination of a degradation calculation is performed in the external device. If the amount of change is determined to be not meeting the criteria, then return to the light sensing step to continue generating a detection value and calculation of the amount of change in absorbance. On the contrary, if the amount of change meets the criteria, then a screen of the external device displays rinsing is complete, and the light source and the pump are stopped, and the detection is stopped. In addition, the result of change in absorbance can also be displayed on the screen of the external device in texts or graphics.

In conclusion, the residual toxicant detection system according to the present disclosure can be used in conjunction with a fruit and vegetable rinsing machine to determine whether the removal of residual toxicants has terminated through the light sensing mechanism. By continuous detection, when the change in absorbance of the aqueous solution containing the residual toxicants is less than the threshold, this implies the fruit/vegetable might be clean. However, in order to avoid misjudgment, only when the event of the change in absorbance is less than the threshold occurs a predetermined number of times before the removal of residual toxicants on the fruit/vegetable has stopped can be confirmed. Existing detection techniques require quantitative sampling, qualitative analysis and a large database for quantitative analysis. On the contrary, the present disclosure has a simple detection procedure, and the continuous detection method makes the result more accurate, and more importantly, it can be used in conjunction with household fruit and vegetable rinsing machines at low cost.

The above embodiments are only used to illustrate the principles of the present disclosure, and should not be construed as to limit the present disclosure in any way. The above embodiments can be modified by those with ordinary skill in the art without departing from the scope of the present disclosure as defined in the following appended claims.

What is claimed is:

1. A residual toxicant detection system, comprising:
   a light source module including at least one light source emitter and at least one light sensor, wherein the at least one light source emitter emits a light having a specific wavelength range;
   a detection portion including an inlet, an outlet and a cavity, allowing an aqueous solution containing a residual toxicant to flow into the inlet, pass through the cavity and flow out of the outlet for the residual toxicant to react with the light having the specific wavelength range, wherein the at least one light sensor is configured to receive the light having the specific wavelength range that passes through the cavity at a plurality of times to produce a plurality of sensing signals, respectively; and
   a processing module configured to calculate an amount of change in absorbances of the aqueous solution respectively based on the sensing signals, wherein when the amount of change in the absorbances of the aqueous solution is less than a threshold, the processing module increases an accumulated detection count, and when the accumulated detection count is greater than or equal to a predetermined value, the processing module produces a detection result.

2. The residual toxicant detection system of claim 1, wherein the processing module includes:
   a driving unit configured to drive the at least one light source emitter to be turned on or turned off;
   a reading unit configured to read the sensing signal at a fixed time interval;
   a memory unit configured to store the sensing signal; and
   a calculation unit configured to calculate the amount of change in absorbance based on the sensing signal and a preset calibration value to produce the detection result.

3. The residual toxicant detection system of claim 2, wherein the calculation unit is configured to generate a removal termination signal based on the detection result.

4. The residual toxicant detection system of claim 1, wherein the processing module includes a transmission unit configured to transmit the detection result to an external device.

5. The residual toxicant detection system of claim 1, wherein the processing module includes a display unit configured to display the detection result.

6. The residual toxicant detection system of claim 1, wherein the at least one light source emitter is plural, and the light emitted by the light source emitters has different specific wavelength ranges.

7. The residual toxicant detection system of claim 1, wherein the specific wavelength range is from 220 nm to 240 nm, from 250 nm to 270 nm, or from 270 nm to 290 nm.

8. The residual toxicant detection system of claim 1, wherein the inlet of the detection portion is connected to a container.

9. The residual toxicant detection system of claim 8, wherein the container contains an object to be tested that contains the residual toxicant with the aqueous solution containing the residual toxicant flowing out of the container.

10. The residual toxicant detection system of claim 8, further comprising a pump provided between the container and the outlet and configured to guide the aqueous solution containing the residual toxicant towards the inlet.

11. The residual toxicant detection system of claim 1, further comprising a power supply module connected with the processing module and configured to provide power for operating the processing module.

12. The residual toxicant detection system of claim 1, wherein the at least one light source emitter and the at least one light sensor are provided at two sides of the cavity, respectively.

13. The residual toxicant detection system of claim 1, wherein the processing module is further configured to produce the detection result when the amount of change in absorbance of the aqueous solution is continuously less than the threshold a predetermined number of times.

14. A method for detecting a residual toxicant, comprising:
    allowing an aqueous solution containing the residual toxicant to flow into a detection portion including a cavity;
    providing at one side of the cavity a light having a specific wavelength range to react with the residual toxicant;
    receiving the light having the specific wavelength range at another side of the cavity at a plurality of times to produce a plurality of sensing signals, respectively; and
    calculating an amount of change in absorbances of the aqueous solution respectively based on the sensing signals, wherein when the amount of change in the absorbances of the aqueous solution is less than a threshold, an accumulated detection count is increased, and when the accumulated detection count is greater than or equal to a predetermined value, a detection result is produced.

15. The method of claim 14, further comprising, after producing the detection result, generating a removal termination signal based on the detection result.

16. The method of claim 14, further comprising, after producing the detection result, transmitting the detection result to an external device or displaying the detection result.

17. The method of claim 14, wherein the light includes a plurality of light having different specific wavelength ranges.

18. The method of claim 14, wherein the specific wavelength range is from 220 nm to 240 nm, from 250 nm to 270 nm, or from 270 to 290 nm.

19. The method of claim 14, wherein the aqueous solution containing the residual toxicant comes from a container in which an object to be tested containing the residual toxicant is placed.

20. The method of claim 14, further comprising producing the detection result when the amount of change in absorbance of the aqueous solution is continuously less than the threshold a predetermined number of times.

21. The residual toxicant detection system of claim 1, wherein the amount of change in the absorbances is a value of each absorbance subtracted from an average of the absorbances.

22. The residual toxicant detection system of claim 1, wherein at the plurality of times, the aqueous solution is continuously flowing through the cavity.

23. The method of claim 14, wherein the amount of change in the absorbances is a value of each absorbance subtracted from an average of the absorbances.

24. The method of claim 14, wherein at the plurality of times, the aqueous solution is continuously flowing through the cavity.

* * * * *